US00PP28243P3

(12) United States Plant Patent
Kientzler

(10) Patent No.: US PP28,243 P3
(45) Date of Patent: Aug. 1, 2017

(54) ***CALIBRACHOA* PLANT NAMED 'USCALCHSTM'**

(50) Latin Name: ***Calibrachoa* sp.**
Varietal Denomination: USCALCHSTM

(71) Applicant: PLANT 21 LLC, Bonsall, CA (US)

(72) Inventor: Helmut Kientzler, Gensingen (DE)

(73) Assignee: PLANT 21 LLC, Bonsall, CA (US)

( * ) Notice: Subject to any disclaimer, the term of this patent is extended or adjusted under 35 U.S.C. 154(b) by 0 days.

(21) Appl. No.: 14/756,445

(22) Filed: Sep. 4, 2015

(65) Prior Publication Data

US 2017/0071117 P1 Mar. 9, 2017

(51) Int. Cl.
*A01H 5/02* (2006.01)

(52) U.S. Cl.
USPC ..... Plt./413

(58) Field of Classification Search
USPC ..... Plt./413
See application file for complete search history.

(56) References Cited

U.S. PATENT DOCUMENTS

PP26,272 P2 12/2015 Westhoff

OTHER PUBLICATIONS

PLUTO Plant Variety Database Aug. 10, 2016, 2 pages.*
Community Plant Variety Office Application No. 2014/1380, filed May 19, 2014 (no fee required per Office action, p. 4-5).
Canada Plant Breeders' Rights Application No. 15/8547, filed Mar. 26, 2016 (no fee required per Office action, p. 4-5).
Gartenbau und Specialkulturen Westhoff GBR and Westhoff Vertriebsgesellschaft MBH, "Complaint," U.S. District Court for the Western District of Pennsylvania, Case No. 2:16-cv-00554, filed May 4, 2016.

* cited by examiner

*Primary Examiner* — Annette Para
(74) *Attorney, Agent, or Firm* — Hauptman Ham, LLP; Rachel K. Pilloff; Sean A. Passino

(57) ABSTRACT

A new and distinct *Calibrachoa* plant named 'USCALCHSTM', characterized by its compact, upright to outwardly spreading and mounding to eventually trailing plant habit; vigorous growth habit; freely branching habit; dense and bushy appearance; freely flowering habit; bright yellow-colored petals with red purple-colored speckles and splotches forming a star-shaped pattern; and good garden performance.

1 Drawing Sheet

Botanical designation: *Calibrachoa* sp.
Cultivar denomination: 'USCALCHSTM'.

BACKGROUND OF THE INVENTION

The present invention relates to a new and distinct cultivar of *Calibrachoa* plant, botanically known as *Calibrachoa* sp. and hereinafter referred to by the name 'USCALCHSTM'.

The new *Calibrachoa* plant is a naturally-occurring whole plant mutation of 'USCAL91001', disclosed in U.S. Plant Pat. No. 23,232. The new *Calibrachoa* plant was discovered and selected by the Inventor as a single flowering plant within a population of plants of 'USCAL91001' in a controlled greenhouse environment in Gensingen, Germany in July, 2012. The selection of the new *Calibrachoa* plant was based on its unique combination of flower color and flower color pattern.

Asexual reproduction of the new *Calibrachoa* plant by vegetative terminal cuttings in a controlled greenhouse environment in Gensingen, Germany since August, 2012 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'USCALCHSTM'. These characteristics in combination distinguish 'USCALCHSTM' as a new and distinct *Calibrachoa* plant:

1. Compact, upright to outwardly spreading and mounding to eventually trailing plant habit.
2. Vigorous growth habit.
3. Freely branching habit; dense and bushy appearance.
4. Freely flowering habit.
5. Bright yellow-colored petals with red purple-colored speckles and splotches forming a star-shaped pattern.
6. Good garden performance.

The new *Calibrachoa* plant can be compared to plants of the mutation parent, 'USCAL91001'. Plants of the new *Calibrachoa* differ primarily from plants of 'USCAL91001' in flower color as plants of 'USCAL91001' have red purple-colored flowers with yellow-colored star-shaped pattern.

Plants of the new *Calibrachoa* can be compared to plants of the *Calibrachoa* sp. 'USCAL23101', disclosed in U.S. Plant Pat. No. 27,010. In side-by-side comparisons conducted in Bonsall, Calif., plants of the new *Calibrachoa* differed primarily from plants of 'USCAL23101' in flower color as plants of 'USCAL23101' had solid cherry red-colored flowers.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'USCALCHSTM' grown in a container.

The photograph at the top of the sheet is a close-up view of a typical flowering plant of 'USCALCHSTM'.

DETAILED BOTANICAL DESCRIPTION

The aforementioned photographs and following observations, measurements and values describe plants grown during the late spring in 10-cm containers in an outdoor nursery in Bonsall, Calif. During the production of the plants, day temperatures averaged 24° C., night temperatures averaged 16° C. and light levels ranged from 7,000 to 10,000 foot-candles. Plants were pinched one time and were nine weeks old when the photographs and description were taken. In the following description, color references are made to The Royal Horticultural Society Colour Chart, 2007 Edition, except where general terms of ordinary dictionary significance are used.

Botanical classification: *Calibrachoa* sp. 'USCALCHSTM'.

Parentage: Naturally-occurring whole plant mutation of 'USCAL91001', disclosed in U.S. Plant Pat. No. 23,232.

Propagation:

*Type.*—By vegetative terminal cuttings.

*Time to initiate roots, summer.*—About four days at temperatures ranging from 17° C. to 29° C.

*Time to initiate roots, winter.*—About six days at temperatures ranging from 17° C. to 21° C.

*Time to produce a rooted plant, summer.*—About 22 days at temperatures ranging from 17° C. to 29° C.

*Time to produce a rooted plant, winter.*—About 25 days at temperatures ranging from 17° C. to 21° C.

*Root description.*—Medium in thickness, fibrous; typically white in color, actual color of the roots is dependent on substrate composition, water quality, fertilizer type and formulation, substrate temperature and physiological age of roots.

*Rooting habit.*—Freely branching; medium density.

Plant description:

*Plant and growth habit.*—Compact, upright to outwardly spreading and mounding to eventually trailing plant habit; freely branching habit with about three primary lateral branches each with multiple secondary branches; pinching enhances branching; dense and bushy appearance; vigorous growth habit.

*Plant height.*—About 9.5 cm.

*Plant diameter.*—About 20 cm.

Lateral branch description:

*Length.*—About 12 cm.

*Diameter.*—About 2 mm.

*Internode length.*—About 1.7 cm.

*Strength.*—Strong.

*Aspect.*—Initially upright then outwardly spreading to eventually trailing.

*Texture.*—Pubescent; minute.

*Color.*—Close to 146C.

Leaf description:

*Arrangement.*—Before flowering, alternate; after flowering, opposite; leaves simple.

*Length.*—About 2.8 cm.

*Width.*—About 1.5 cm.

*Shape.*—Elliptical.

*Apex.*—Rounded to broadly acute.

*Base.*—Attenuate.

*Margin.*—Entire.

*Texture, upper and lower surfaces.*—Pubescent; minute.

*Luster, upper and lower surfaces.*—Matte.

*Venation pattern.*—Pinnate; arcuate.

*Color.*—Developing leaves, upper surface: Close to N137C. Developing leaves, lower surface: Close to 146A. Fully expanded leaves, upper surface: Close to N137B; venation, close to 146B. Fully expanded leaves, lower surface: Close to 146A; venation, close to 146B.

*Petioles.*—Length: About 4 mm. Diameter: About 2 mm. Texture, upper and lower surfaces: Pubescent; minute. Color, upper and lower surfaces: Close to 146C.

Flower description:

*Flower type and flowering habit.*—Single salverform flowers arising from leaf axils; freely flowering habit with typically about six to eight open flowers per lateral branch and more than 100 open flowers per plant at a time; flowers face upright to outwardly.

*Fragrance.*—None detected.

*Natural flowering season.*—Plants of the new *Calibrachoa* begin flowering about four weeks after planting; plants flower continuously from the early spring though the summer until autumn in Southern California.

*Flower longevity.*—Individual flowers last about five to seven days on the plant; flowers persistent.

*Flower buds.*—Length: About 2.3 cm. Diameter: About 8 mm. Shape: Oblong, elongate. Color: Close to 1C.

*Flower diameter.*—About 3.4 cm by 2.7 cm.

*Flower length (height).*—About 2.7 cm.

*Flower throat diameter.*—About 5 mm by 8 mm.

*Flower tube length.*—About 1.8 cm.

*Flower tube diameter, base.*—About 2.5 mm.

*Corolla.*—Arrangement: Five fused petals opening into a flared trumpet. Petal lobe length (from throat): About 1.4 cm. Petal lobe width: About 1.6 cm. Petal shape: Fan-shaped. Petal apex: Rounded, slightly and shallowly emarginate. Petal margin: Entire. Petal texture, upper surface: Smooth, glabrous; velvety. Petal texture, lower surface: Pubescent; minute and primarily along the veins. Throat texture: Smooth, glabrous. Tube texture: Pubescent; minute and primarily along the veins. Petal luster, upper and lower surfaces: Matte. Throat luster: Glossy. Tube luster:

Matte. Color: Petal lobe, when opening, upper surface: Close to 2B; centers, irregular speckles and splotches, close to 71A. Petal lobe, when opening, lower surface: Close to 2D; centers, irregular splotches and speckles, close to 186B. Petal lobe, fully opened, upper surface: Close to 3B; centers, irregular speckles and splotches, close to 61A; venation, close to 3B; with development, ground color becoming closer to 4D and speckles and splotches becoming closer to 71A to 71B. Petal lobe, fully opened, lower surface: Close to 3D; centers, irregular splotches and speckles, close to 186A; venation, closer to N77A. Throat: Close to 9A; venation, close to 1B. Tube: Close to 3D; venation, close to N77A.

*Calyx.*—Arrangement: One star-shaped calyx tube with five sepals fused towards the base and arranged in a single whorl. Sepal length: About 1.2 cm. Sepal width: About 3 mm. Sepal shape: Narrowly elliptic. Sepal apex: Acute. Sepal margin: Entire. Sepal texture, upper and lower surfaces: Pubescent; minute. Sepal color, upper surface: Close to 146A to 146B. Sepal color, lower surface: Close to 146B.

*Peduncles.*—Length: About 1.2 cm. Diameter: About 1.5 mm. Angle: About 45° from stem axis. Strength: Strong. Texture: Pubescent; minute. Color: Close to 146C.

*Reproductive organs.*—Stamens: Quantity: Five per flower. Filament length: About 6 mm. Filament color: Close to 145D. Anther length: About 1 mm. Anther shape: Oval. Anther color: Close to 10B. Pollen amount: Scarce. Pollen color: Close to 10A. Pistils: Quantity: One per flower. Pistil length: About 1.2 cm. Style length: About 8 mm. Style color: Close to 145C. Stigma shape: Round. Stigma color: Close to 146D. Ovary color: Close to 145B. Seeds and fruits: Seed and fruit development have not been observed on plants of the new *Calibrachoa.*

Garden performance: Plants of the new *Calibrachoa* have been observed to have good garden performance and tolerate wind, rain and temperatures ranging from about 1° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'USCALCHSTM' as illustrated and described.

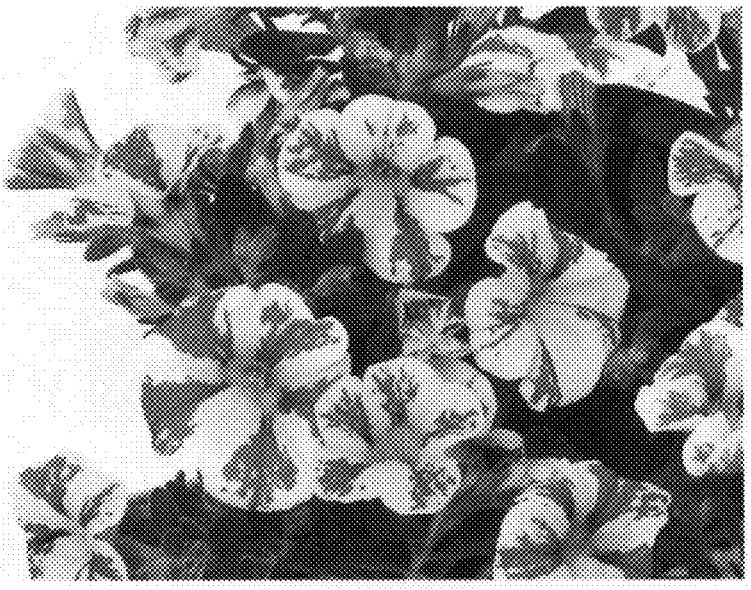
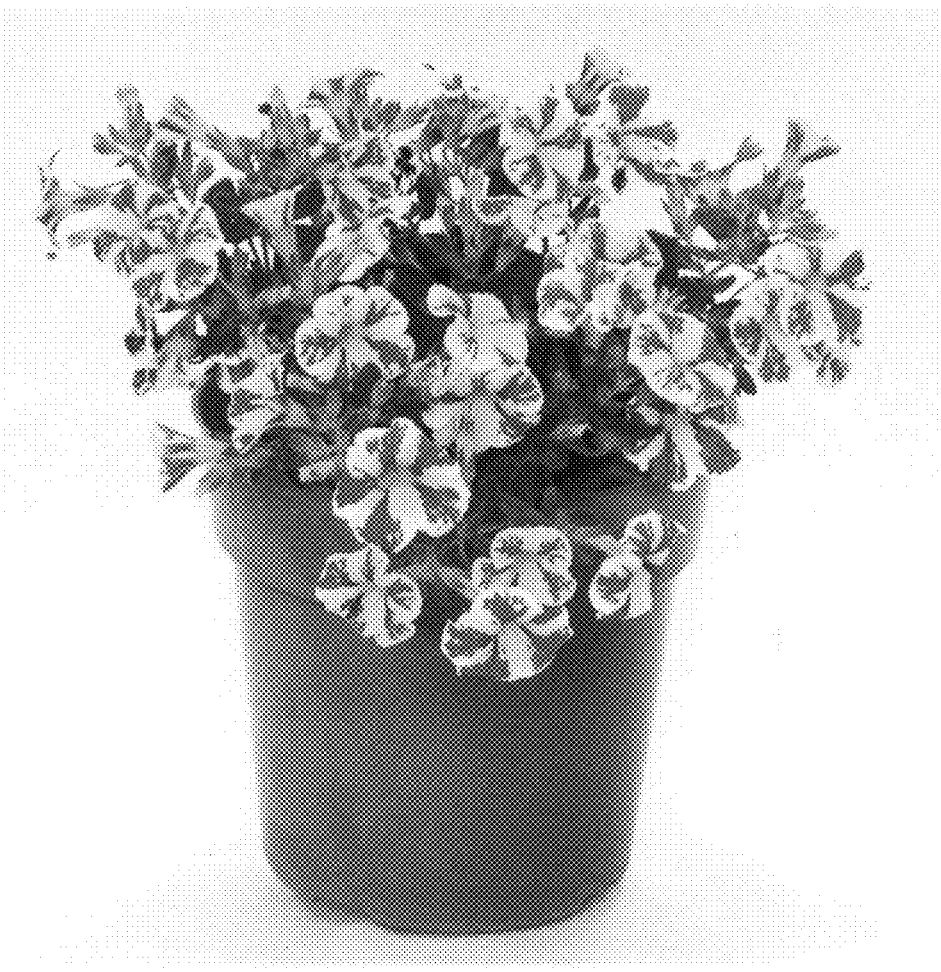

* * * * *